(12) United States Patent
Snyder et al.

(10) Patent No.: US 9,725,278 B2
(45) Date of Patent: Aug. 8, 2017

(54) METHOD AND APPARATUS FOR FORMING A KNOT IN SURGICAL SUTURE OR OTHER FILAMENT

(71) Applicant: Redyns Medical LLC, Los Angeles, CA (US)

(72) Inventors: Nathan B. Snyder, Los Angeles, CA (US); Stephen J. Snyder, Encino, CA (US); Ronald Litke, Sandy Hook, CT (US)

(73) Assignee: Redyns Medical LLC, Los Angeles, CA (US)

( * ) Notice: Subject to any disclaimer, the term of this patent is extended or adjusted under 35 U.S.C. 154(b) by 968 days.

(21) Appl. No.: 13/767,790

(22) Filed: Feb. 14, 2013

(65) Prior Publication Data

US 2013/0211429 A1    Aug. 15, 2013

Related U.S. Application Data

(60) Provisional application No. 61/598,450, filed on Feb. 14, 2012.

(51) Int. Cl.
*B65H 69/04* (2006.01)
*A61B 17/06* (2006.01)
*A61B 17/00* (2006.01)
*A61B 17/04* (2006.01)

(52) U.S. Cl.
CPC .............. *B65H 69/04* (2013.01); *A61B 17/06* (2013.01); *A61B 17/06166* (2013.01); *B65H 69/043* (2013.01); *A61B 2017/00526* (2013.01); *A61B 2017/0475* (2013.01); *A61B 2017/0477* (2013.01)

(58) Field of Classification Search
CPC .............. A61B 17/06166; A61B 17/06; A61B 2017/0477; A61B 2017/0475; A61B 2017/00526; A61B 2017/0474; A61B 2017/0482; A61B 2017/0483; A61B 2017/0485; A61B 17/0482; A61B 17/0483; A61B 17/0485; B65H 69/04; B65H 69/043
See application file for complete search history.

(56) References Cited

U.S. PATENT DOCUMENTS

| | | | |
|---|---|---|---|
| 876,573 A * | 1/1908 | Myers ................ | B65H 69/043 140/101 |
| 2008/0315023 A1* | 12/2008 | Orko .................... | B65H 69/043 242/157 R |

* cited by examiner

*Primary Examiner* — Ryan J Severson
*Assistant Examiner* — Christian Knauss
(74) *Attorney, Agent, or Firm* — Pandiscio & Pandiscio

(57) ABSTRACT

Apparatus for forming a knot, the apparatus having a first pathway for receiving a first element, and a second pathway for receiving a second element, the first pathway having a configuration which corresponds to the path to be followed by the first element and the second pathway having a configuration which corresponds to the path to be followed by the second element, respectively, in order to form a knot; a shuttle for moving the second element; and a mechanism for moving the shuttle through the second pathway, whereby, when the first element is received in the first pathway and the second element is connected to the shuttle, movement of the shuttle through the second pathway causes the second element to be moved through the second pathway so as to form a knot around the first element.

11 Claims, 14 Drawing Sheets

METHOD AND APPARATUS FOR FORMING A KNOT IN SURGICAL SUTURE OR OTHER FILAMENT

REFERENCE TO PRIOR PATENT APPLICATION

This patent application claims benefit of prior U.S. Provisional Patent Application Ser. No. 61/598,450, filed Feb. 14, 2012 by Nathan B. Snyder et al. for SURGICAL SUTURE TYING DEVICE AND SURGICAL TECHNIQUE, which patent application is hereby incorporated herein by reference.

FIELD OF THE INVENTION

This invention relates to surgical methods and apparatus in general, and more particularly to a method and apparatus for forming a knot in surgical suture. This invention also relates to forming a knot in filaments other than surgical suture.

BACKGROUND OF THE INVENTION

The field of surgery includes both open and arthroscopic procedures. One common technique for most repair or reconstruction procedures is that one or more strands of suture material are used to repair torn soft tissue, or to reattach soft tissue back to bone, so that the anatomy will heal. A critical element of this "suture repair" is the need to tie the ends of the sutures together to form a knot.

Currently, in some scenarios in which a surgeon ties a knot intra-operatively, a surgeon must develop the skill and dexterity to fashion a knot in the ends of the sutures, pass that knot down to the level of the needed repair, tighten the knot and lock the knot so that the knot will maintain proper tension for holding the tissues together for healing. In many cases, the maneuvers required to tie the desired knot are complex and require considerable practice to learn in order to maintain the requisite level of proficiency.

In other instances, in order to save a surgeon from having to tie a knot intra-operatively, manufacturers pre-tie a surgical knot in the suture, and provide a device to deploy the suture to the operative site so that a surgeon does not have to tie the suture knot intra-operatively. Currently, in order to manufacture a suture with a pre-tied surgical knot, a person must first be trained to be proficient in knot tying. This raises the possibility of irregularities in the quality of the manufacturing process as a result of fatigue, distraction or human error.

Accordingly, there is a need for a new and improved method and apparatus for forming a knot in surgical suture which addresses the deficiencies of the prior art.

In addition, knots are frequently used in non-medical applications (e.g., fishing). The formation of these knots can require substantial skill, can be time-consuming and can be prone to error due to fatigue, distraction or human error. Thus, there is a need for a new and improved method and apparatus for forming a knot in filaments which address the deficiencies of the prior art.

SUMMARY OF THE INVENTION

These and other objects are addressed by the provision and use of a novel apparatus for forming a knot in surgical suture, or for forming a knot in other filaments.

In one embodiment of the present invention, there is provided a new, hand-held tool designed to facilitate a surgeon's task of tying a knot using any type of filament or suture material desired. The hand-held tool ensures that perfectly formed knots are developed quickly and easily, with no chance for irregularities. The knots formed with the system of the present invention may include various types of sliding-locking knots and hitches depending on the individual requirement of the surgeon. After a knot is formed by the device of the present invention, the knot may be guided into place, tightened and locked. The efficiency and security provided will save considerable time and ensure consistent, reliable knots in all procedures.

In another embodiment of the present invention, there is provided a table-top device that may be used by a manufacturer to pre-tie a knot in a filament or suture to be provided to a surgeon, thereby providing a surgeon with a pre-tied knot in a filament or suture using any type of filament or suture material desired. Similar to the hand-held device, the table-top device of the present invention forms a knot in suture with no chance for irregularities and at a rate that is superior to current methods.

The aforementioned hand-held tool and/or table-top device may also be used to form knots for non-medical applications.

In one form of the present invention, there is provided apparatus for forming a knot in filament, the apparatus comprising:
a first assembly comprising a shuttle, and a mechanism for advancing and retracting the shuttle; and
a second assembly having a first pathway for passing a first strand of filament and a second pathway for passing a second strand of filament;
wherein the first assembly and the second assembly are connected together so that the shuttle may be passed from the first assembly to the second assembly in order to carry the second strand of filament through the second pathway of the second assembly, thereby forming a knot around the first strand of filament.

In another form of the present invention, there is provided a method for forming a knot in suture, the method comprising:
providing a system comprising:
 a first assembly comprising a shuttle, and a mechanism for advancing and retracting the shuttle; and
 a second assembly having a first pathway for passing a first strand of filament and a second pathway for passing a second strand of filament;
 wherein the first assembly and the second assembly are connected together so that the shuttle may be passed from the first assembly to the second assembly in order to carry the second strand of filament through the second pathway of the second assembly, thereby forming a knot around the first strand of filament;
passing a first strand of filament through the first pathway;
advancing the shuttle into the second pathway;
securing a second strand of filament to the shuttle;
retracting the shuttle, with the second filament of suture attached thereto, through the second pathway so that the second strand of filament is maneuvered around the first strand of filament, thereby forming a knot around the first strand of filament.

In another form of the present invention, there is provided apparatus for forming a knot, the apparatus comprising:
a first pathway for receiving a first element, and a second pathway for receiving a second element, wherein the first pathway and the second pathway have configurations which correspond to the paths to be followed by the first element and the second element, respectively, in order to form a knot;

a shuttle for moving the second element; and a mechanism for moving the shuttle through the second pathway, whereby, when the first element is received in the first pathway and the second element is connected to the shuttle, movement of the shuttle through the second pathway causes the second element to be moved through the second pathway so as to form a knot around the first element.

In another form of the present invention, there is provided a method for forming a knot, the method comprising:

providing apparatus comprising:

a first pathway for receiving a first element, and a second pathway for receiving a second element, wherein the first pathway and the second pathway have configurations which correspond to the paths to be followed by the first element and the second element, respectively, in order to form a knot;

a shuttle for moving the second element; and a mechanism for moving the shuttle through the second pathway, whereby, when the first element is received in the first pathway and the second element is connected to the shuttle, movement of the shuttle through the second pathway causes the second element to be moved through the second pathway so as to form a knot around the first element;

passing the first element through the first pathway;

advancing the shuttle into the second pathway;

securing the second element to the shuttle; and retracting the shuttle, with the second element attached thereto, through the second pathway so that the second element is maneuvered around the first element, thereby forming a knot around the first element.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein.

DETAILED DESCRIPTION OF THE INVENTION

The present invention comprises the provision and use of a novel system for forming a knot in suture or other filament.

More particularly, the system of the present invention may be used to form a sliding knot or a hitch between two filaments of suture or other filament.

A sliding knot or a hitch are generally constructed of two strands. One stand is typically referred to as the "post strand" and the other strand is typically referred to as a "loop strand". The post strand generally maintains a relatively straight form and is typically held under tension so as to enable the loop strand to form a knot around the post strand and eventually slide down the post strand, into the desired position.

Figure 1:
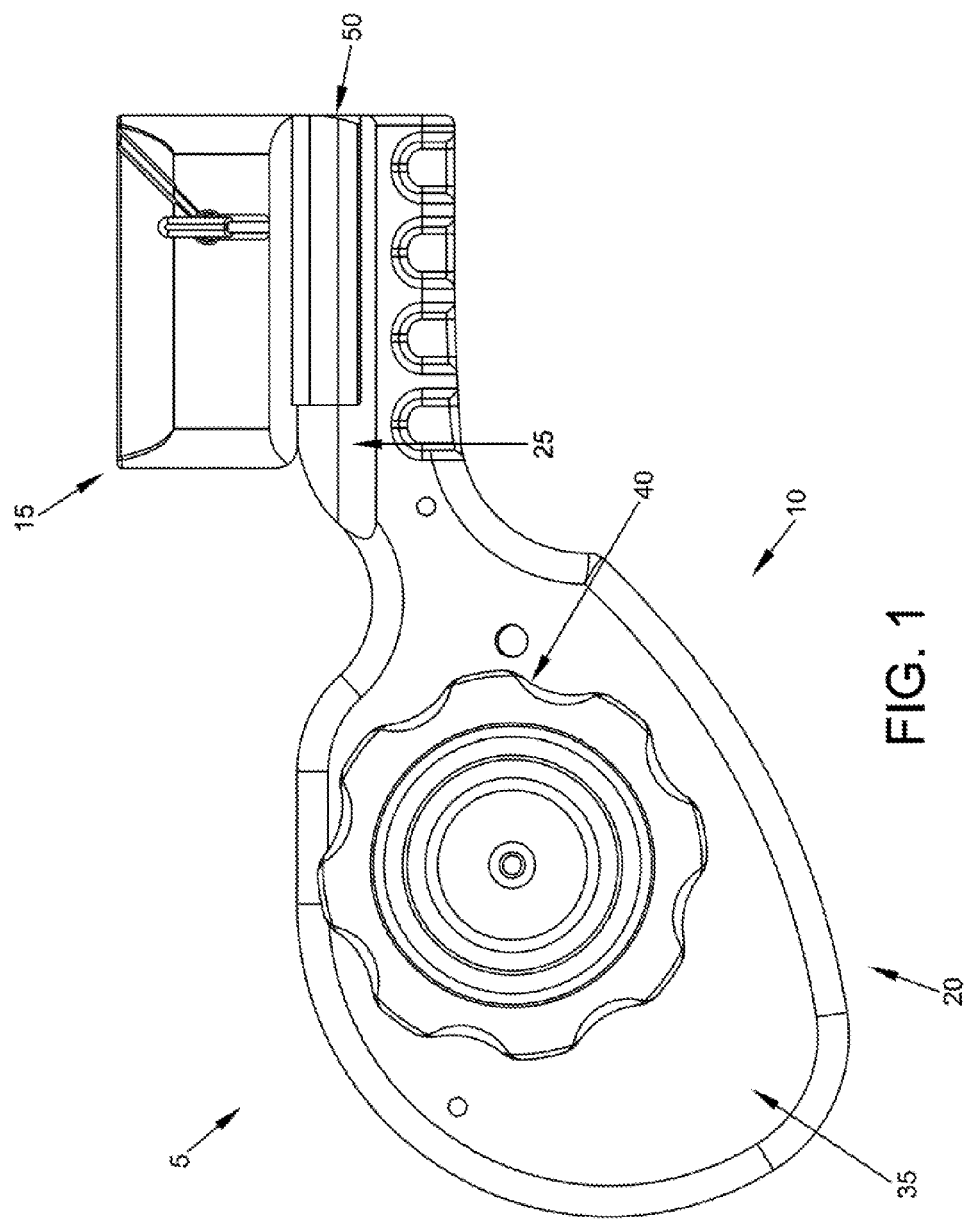
FIG. 1 is a right side schematic view of a novel system for forming a knot in suture, wherein the novel system comprises a hand-held shuttle driver assembly and a knot box.
Figure 1A:
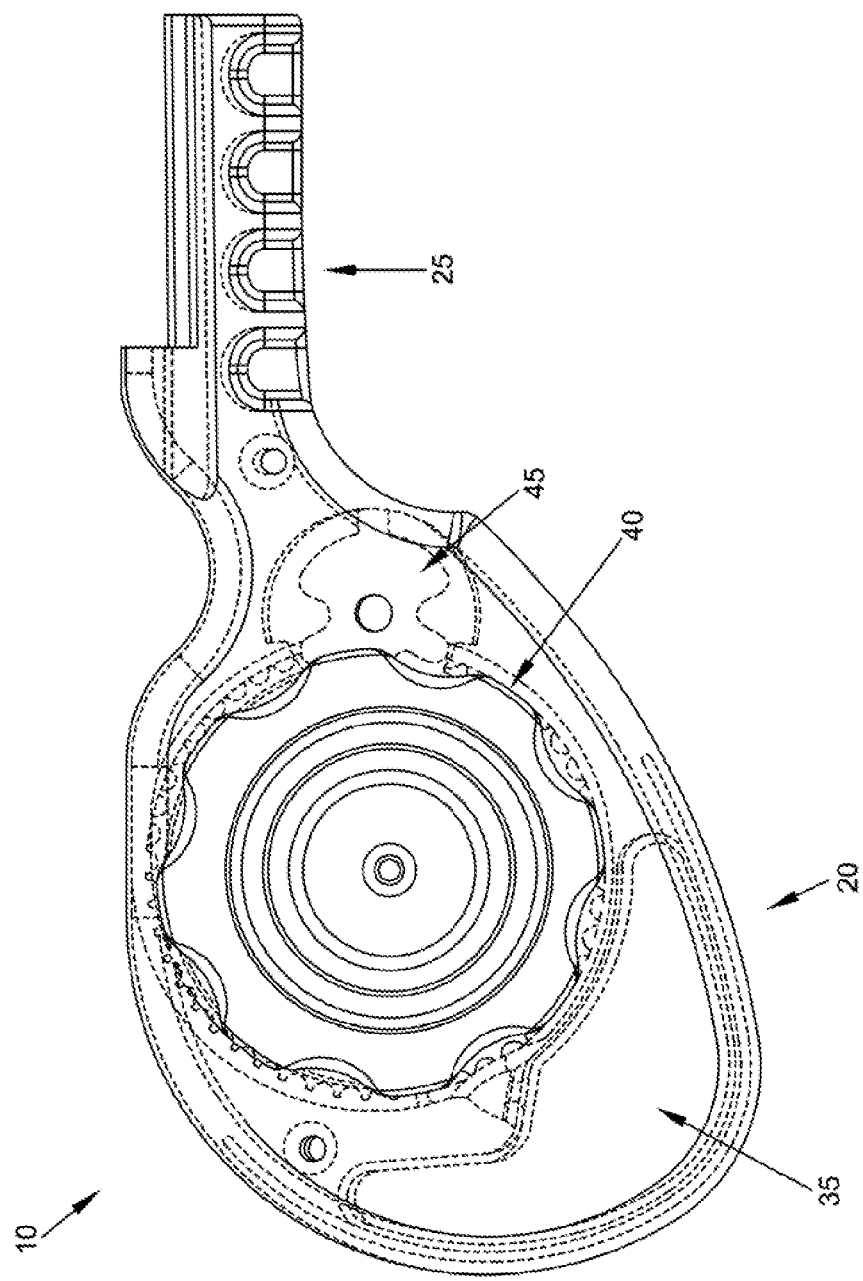
FIG. 1A is a right side schematic view of the shuttle driver assembly of FIG. 1 in which the shuttle driver assembly is transparent.
Figure 2:
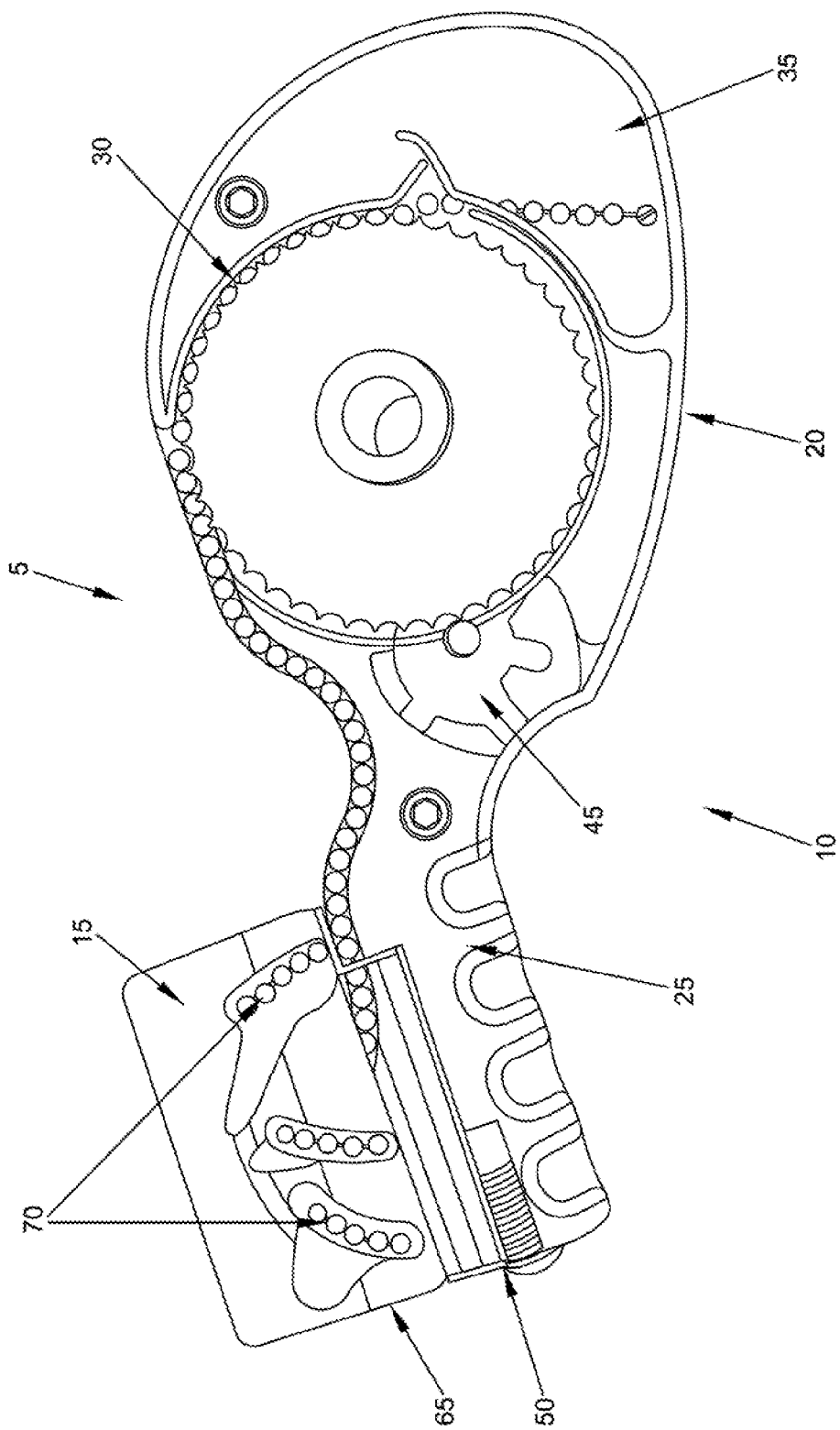
FIG. 2 is a left side view of the novel system of FIG. 1 in which the shuttle driver assembly and knot box are transparent and a shuttle is shown running through a second inner pathway of the knot box.

In one preferred form of the present invention, and looking now at FIGS. 1, 1A and 2, there is a provided a novel system 5 for forming a knot in suture or other filament. Novel system 5 generally comprises a hand-held shuttle driver assembly 10 and a knot box 15.

Shuttle driver assembly 10 comprises a handle portion 20, which may be held in the palm of a left hand, a shaft 25 extending from the handle portion for receiving knot box 15, and a shuttle 30 which is configured to pass from handle portion 20 to shaft 25 and into knot box 15.

Handle portion 20 of shuttle driver assembly 10 comprises a shuttle reservoir 35 for housing shuttle 30 when shuttle 30 is not extended through knot box 15, as will be described in further detail below. Handle portion 20 also comprises a rotary dial 40 for advancing shuttle 30 out of handle portion 20 and into knot box 15 and retrieving shuttle 30 out of knot box 15 and into handle portion 20, and a shuttle travel monitor 45 for controlling how much of shuttle 30 is advanced into, or retrieved from, the knot box 15.

Shaft 30 comprises an attachment mechanism 50 for securing knot box 15 to shuttle driver assembly 10. In one embodiment, attachment mechanism 50 comprises a tongue formed in a top portion of shaft 30 for receipt in a mating groove formed on a bottom portion of knot box 15. In another embodiment, attachment mechanism 50 comprises a groove formed in a top portion of shaft 30 which may receive a mating projection formed on a bottom portion of knot box 15.

Figure 3:
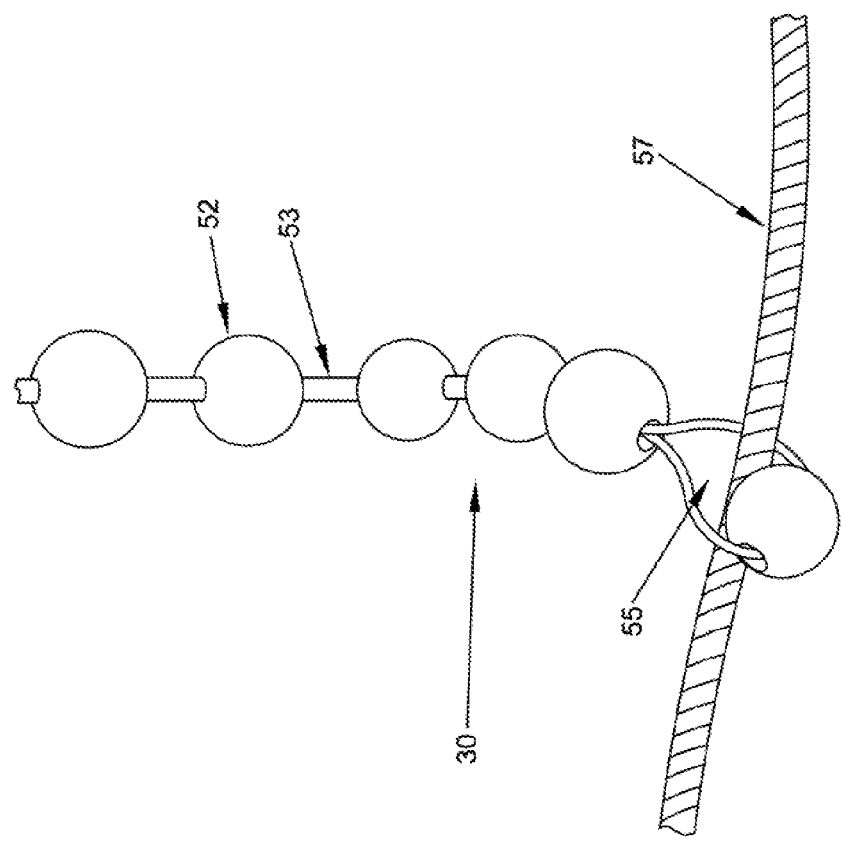
FIG. 3 is a view of an exemplary way of securing a loop strand of filament to a shuttle.

Shuttle 30 is configured to be passed from handle portion 20 through shaft 25 and into knot box 15 and then secured to a loop strand of filament so that the loop strand of filament may be towed into, and through, knot box 15, following a pre-determined path, as will be described in further detail below. In one embodiment, and looking now at FIG. 3, shuttle 30 comprises a strand of spheres 52 connected together by a filament 53, or connected together in some other manner so as to provide a flexible strand of spheres, with a loop or eyelet 55 being formed at one end of shuttle 30. In this embodiment, a loop strand of filament 57 may be secured to shuttle 30 by passing loop strand of filament 57 through eyelet 55.

Figure 4:
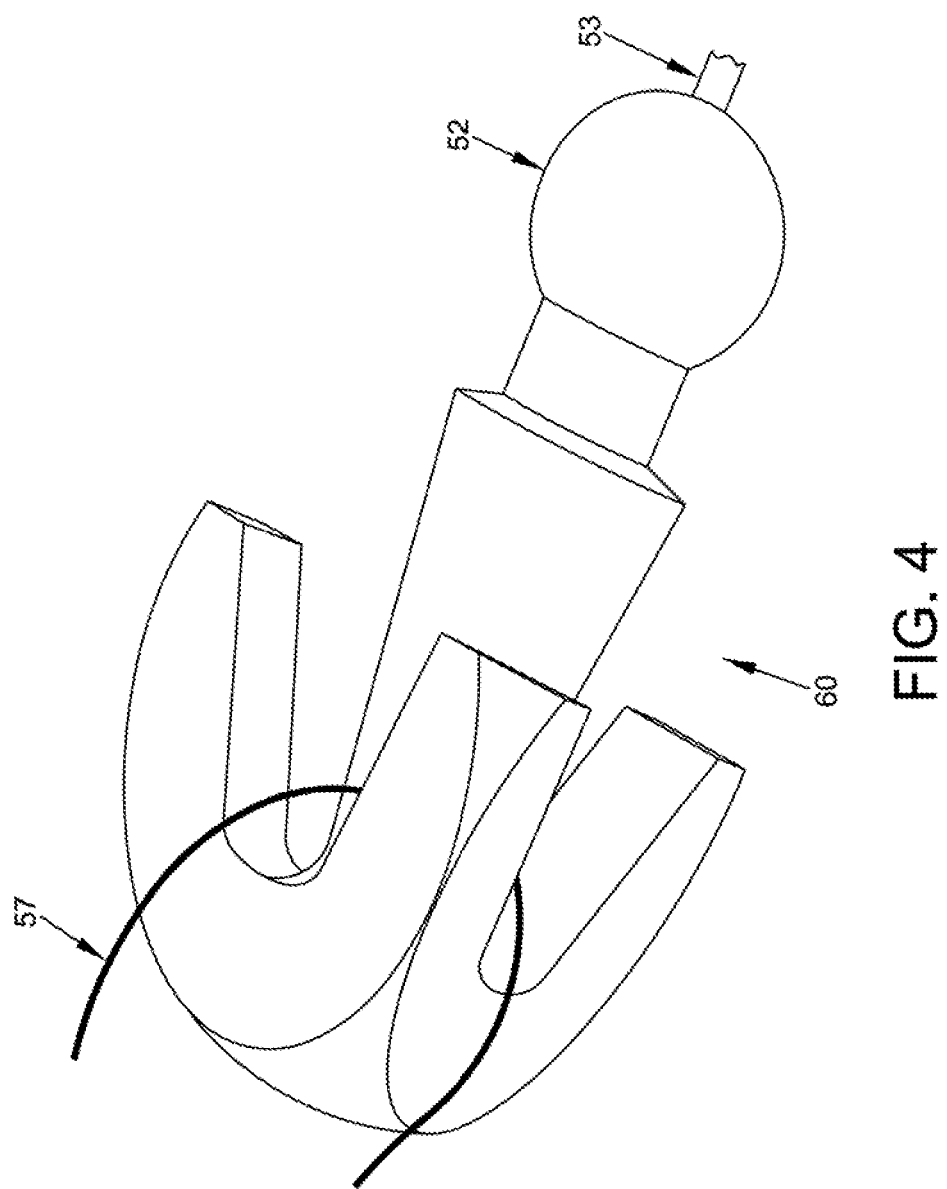
FIG. 4 is a schematic view of a second exemplary way of securing a loop strand of filament to a shuttle.

In another embodiment, and looking now at FIG. 4, shuttle 30 comprises a strand of spheres 52 connected together by a filament 53, or connected together in some other manner so as to provide a flexible strand of spheres, with a three-sided cleat 60 positioned at one end of the shuttle. In this embodiment, three-sided cleat 60 may be used to snag loop strand of filament 57 in order to secure loop strand of filament 57 to shuttle 30.

Figure 5:
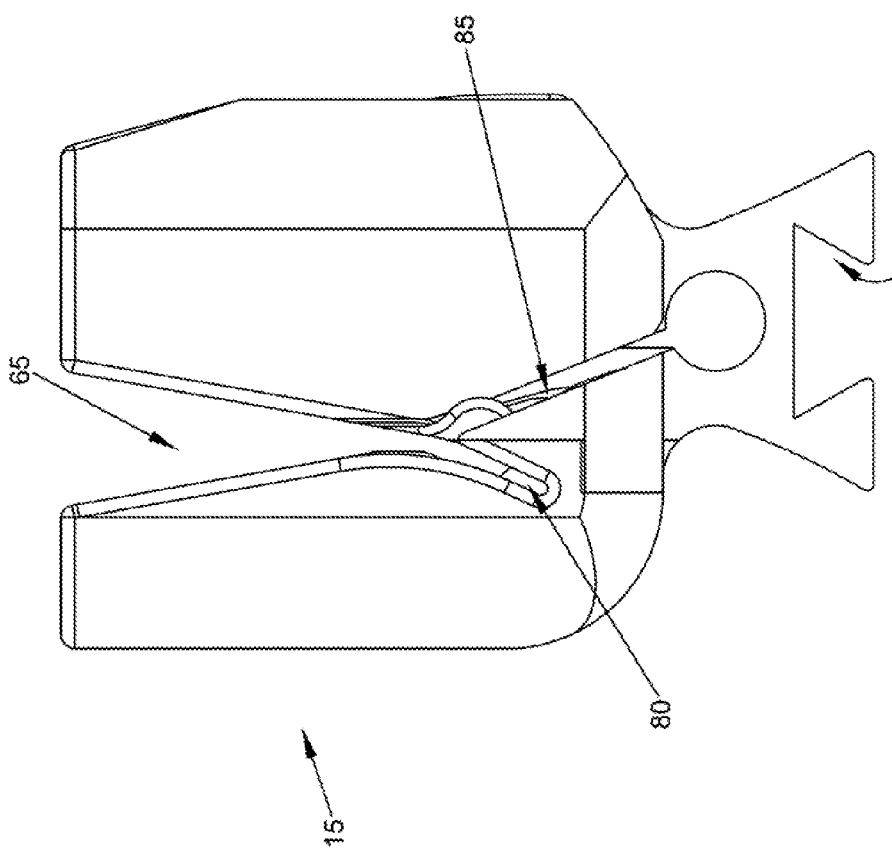
FIGS. 5 and 6 are schematic views showing further details of the knot box of the present invention.
Figure 6:
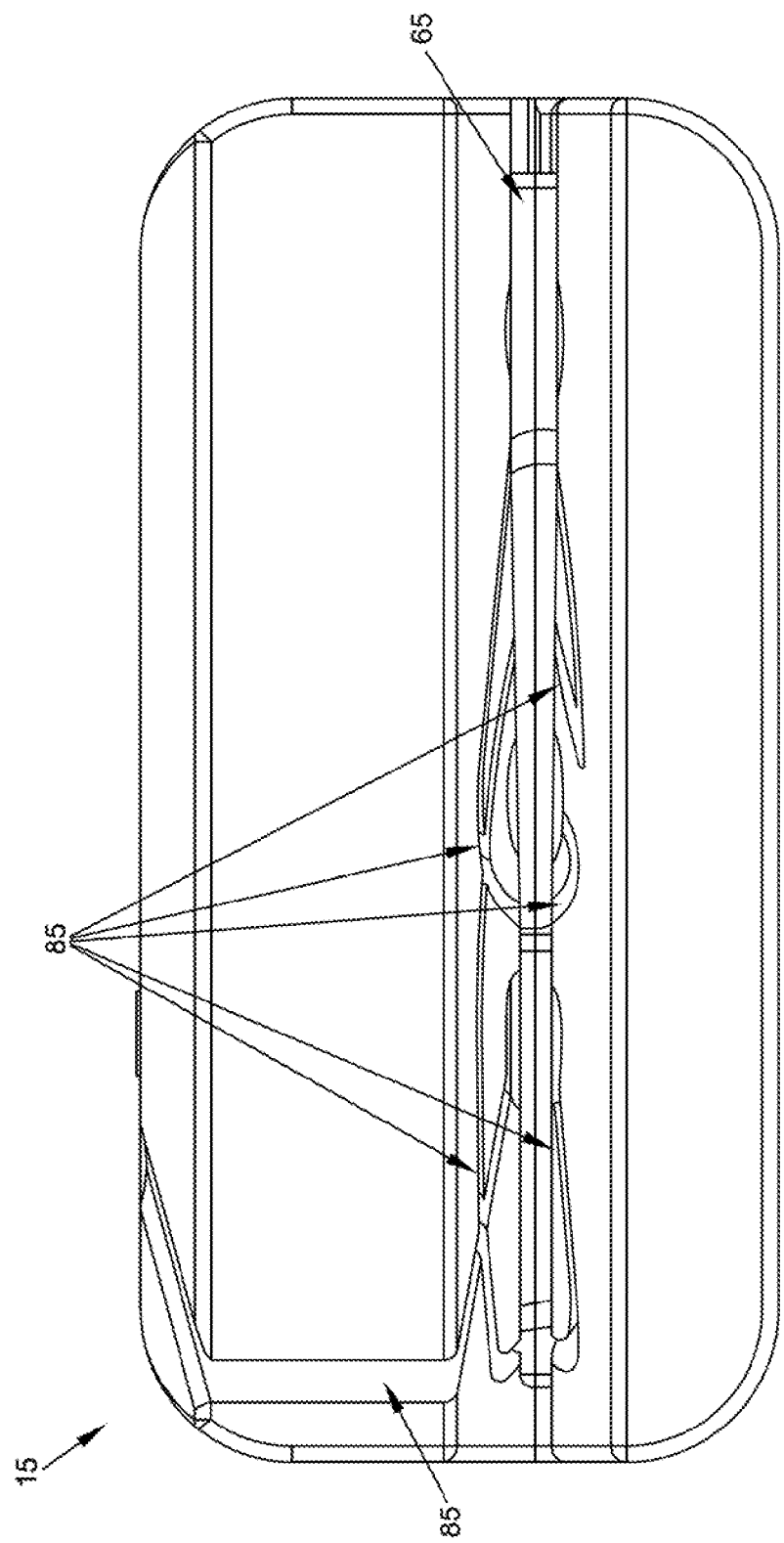

Looking now at FIGS. 2, 5 and 6, knot box 15 comprises a first pathway 65 for passing a post strand of filament, and a second pathway 70 for passing loop strand of filament 57 through the knot box in a pre-determined path around the post strand of filament in order to form a knot in the filament, as will be discussed in further detail below.

As stated above, knot box 15 may also comprise an attachment mechanism 50 for connecting knot box 15 to suture driver assembly 10. In a preferred embodiment, and as shown in FIG. 5, attachment mechanism 50 comprises a dovetail slot formed in a bottom portion of knot box 15 for receiving a mating dovetail projection formed on a top portion of shaft 25 of shuttle driver assembly 10.

First pathway 65, which is intended to receive the post strand of filament, may be formed as a straight cutaway through the center of the long access of the knot box, ending approximately halfway into the thickness of the knot box. First pathway 65 may have one or more small filament-engaging elements 80 located along the length of the straight pathway. These filament-engaging elements 80 are designed to secure the post strand of filament in first pathway 65 as the post strand is positioned in the knot box in preparation for forming the knot.

Second pathway 70, which is intended to mimic the path that the loop strand of filament must travel in order to form the intended knot, may be formed as an interior pathway in knot box 15. Second pathway 70 may be formed in a variety of different patterns which correspond to the direction of travel which must be taken by the loop strand of filament in order to generate an intended knot. Accordingly, various knot boxes may be developed, each with a specific set of patterns formed within the knot box, for use in forming a particular knot in accordance with the present invention.

Second pathway 70 is also formed within knot box 15 so that when loop strand of filament 57 is drawn through the second pathway, as will be described in further detail below, loop strand of filament 57 contacts a specific surface of the second pathway. This specific surface is typically the surface area of the second pathway which, when contacted by loop strand of filament 57, constitutes the shortest path for loop strand of filament 57 through the second pathway.

Furthermore, second pathway 70 comprises an opening 85, also sometimes hereinafter referred to as filament release window 85, which intersects the second pathway at a different location than where loop strand of filament 57 extends when the loop strand of filament is being pulled through the second pathway by shuttle 30, as will be discussed in further detail below. The width of filament release window 85 is specifically sized to be smaller than the width of shuttle 30, but larger than the width of loop strand of filament 57. Filament release window 85 is configured so as to allow loop strand of filament 57 to exit the second pathway once a user fully advances loop strand of filament 57 through the second pathway and desires to remove the newly formed knot from the knot box. In a preferred embodiment, and looking now at FIGS. 5 and 6, first pathway 65 extends through the middle of knot box 15, and various components of filament release window 85 emanate from either side of first pathway 65.

System 5 is preferably used in the following manner to form a knot in filament or suture.

First, a post strand of filament is secured in first pathway 65 of knot box 15. Then shuttle 30 is advanced from shuttle reservoir 35, into and through second pathway 70 via rotation of rotary dial 40 on shuttle driver assembly 10. Next, an end of loop strand of filament 57 is secured to the end of shuttle 30, and then the shuttle is pulled back through the second pathway, thereby towing loop strand of filament 57 through second pathway 70 of knot box 15. As this occurs, loop strand of filament 57 is maneuvered about the post strand of filament in precisely the required pattern in order to form a desired knot on the post strand of suture.

Figure 7:
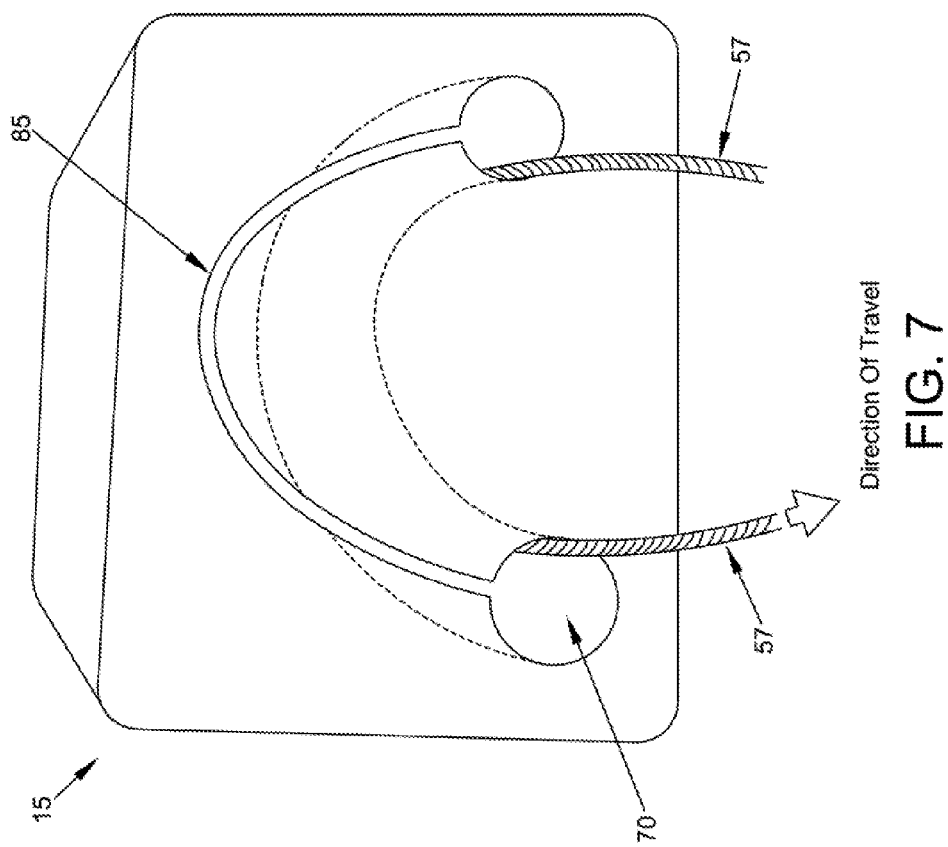
FIG. 7 is a schematic view illustrating the loop strand of filament being pulled through the second pathway of the knot box.

As can be seen in FIG. 7, when tension is applied to the long axis of loop strand of filament 57 as loop strand of filament 57 is pulled through second pathway 70 by shuttle 30, the loop strand of filament 57 follows the aforementioned shortest path through second pathway 70. This ensures that loop strand of filament 57 contacts the surface of second pathway 70 which is separate from filament release window 85, thereby ensuring that loop strand of filament 57 does not inadvertently exit filament release window 85.

Figure 8:
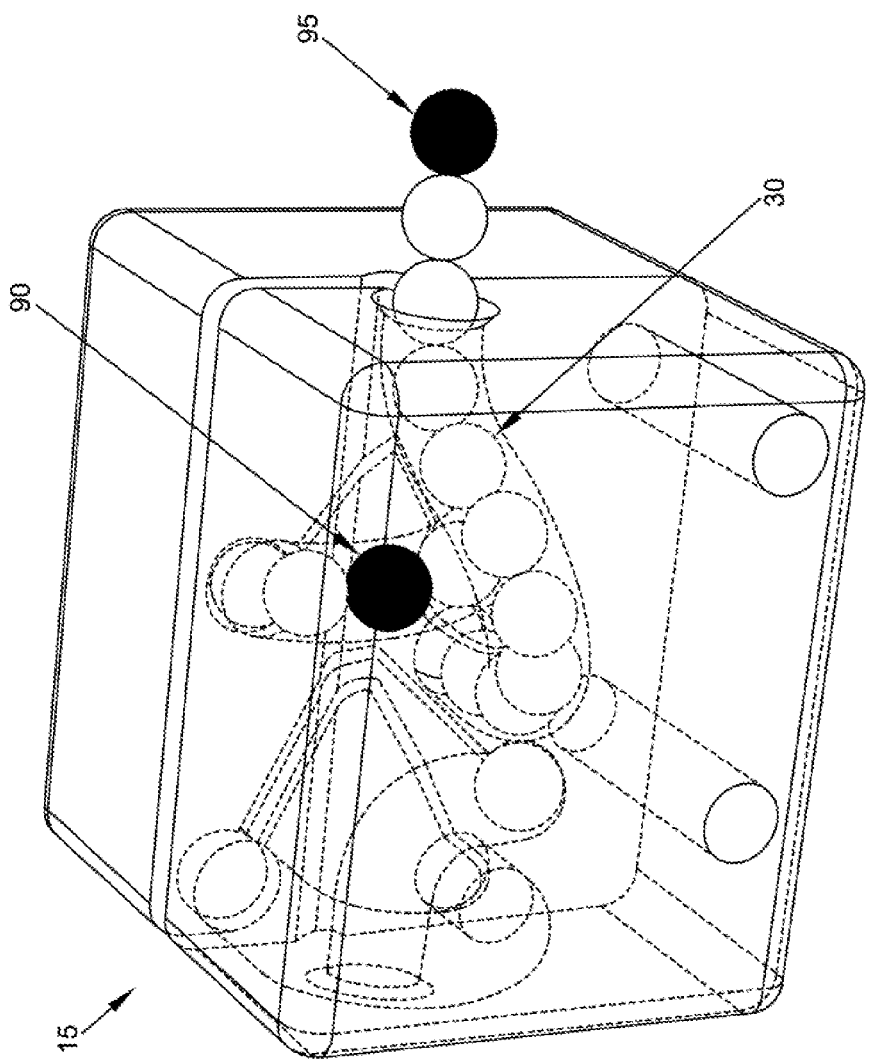
FIGS. 8-10 are schematic views illustrating the progression of a shuttle carrying the loop strand of filament through the second pathway of the knot box.
Figure 9:
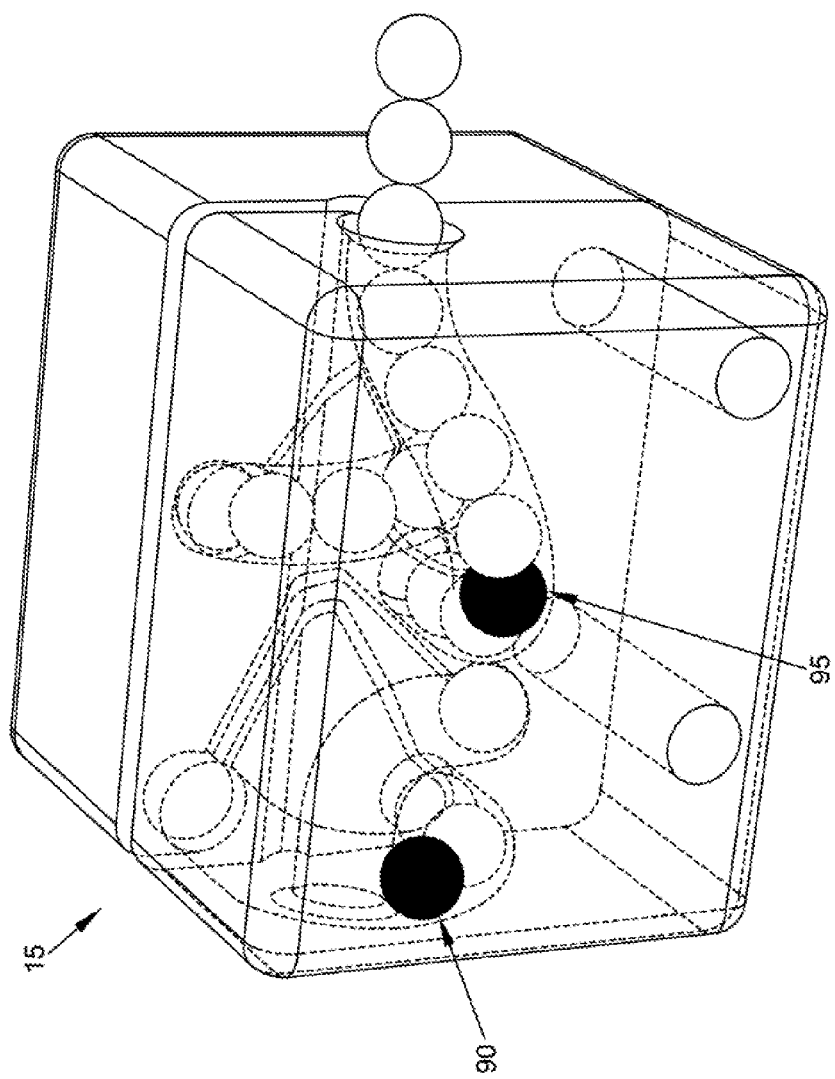
Figure 10:
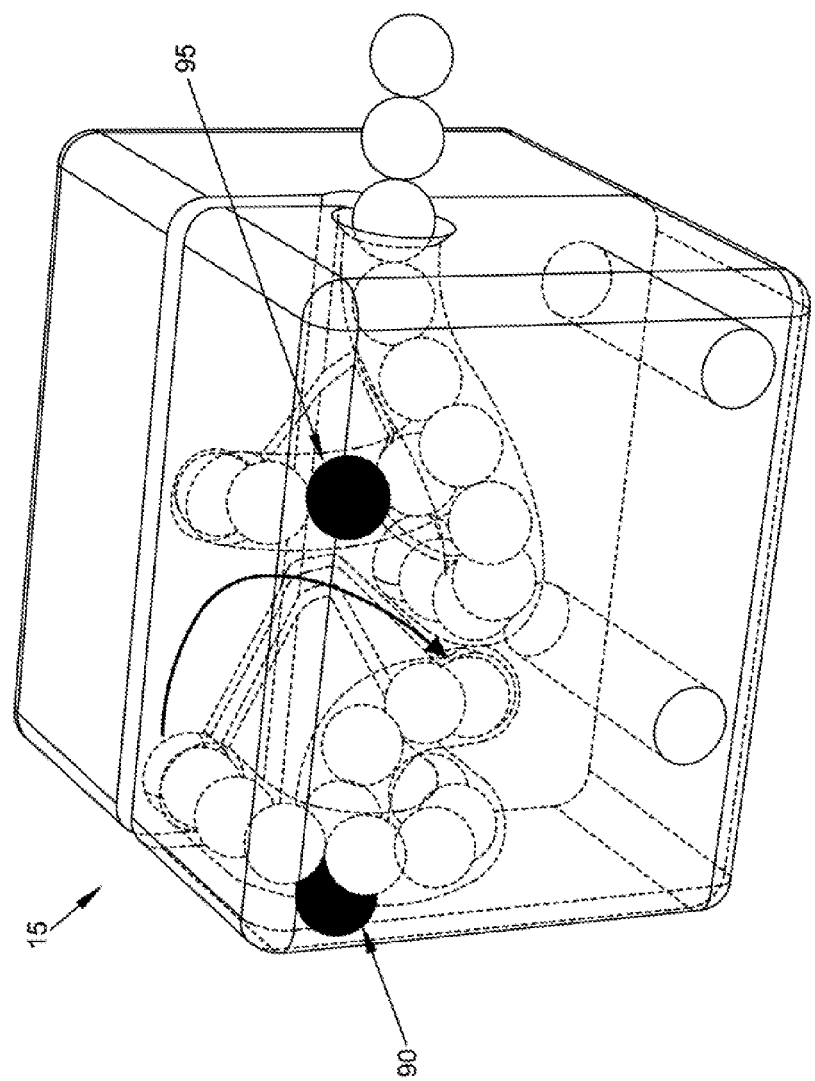

Looking now at FIGS. 8-10, progression of shuttle 30 through an exemplary second pathway 70 is shown in further detail, in which the leading end of shuttle 30 is shown at 90 and the trailing end of shuttle 30 is shown at 95. The pattern of second pathway 70 shown in FIGS. 8-10 results in the formation of a sliding, locking knot as loop strand of filament 57 is passed through second pathway 70 (and hence around the post strand of filament).

Figure 11:
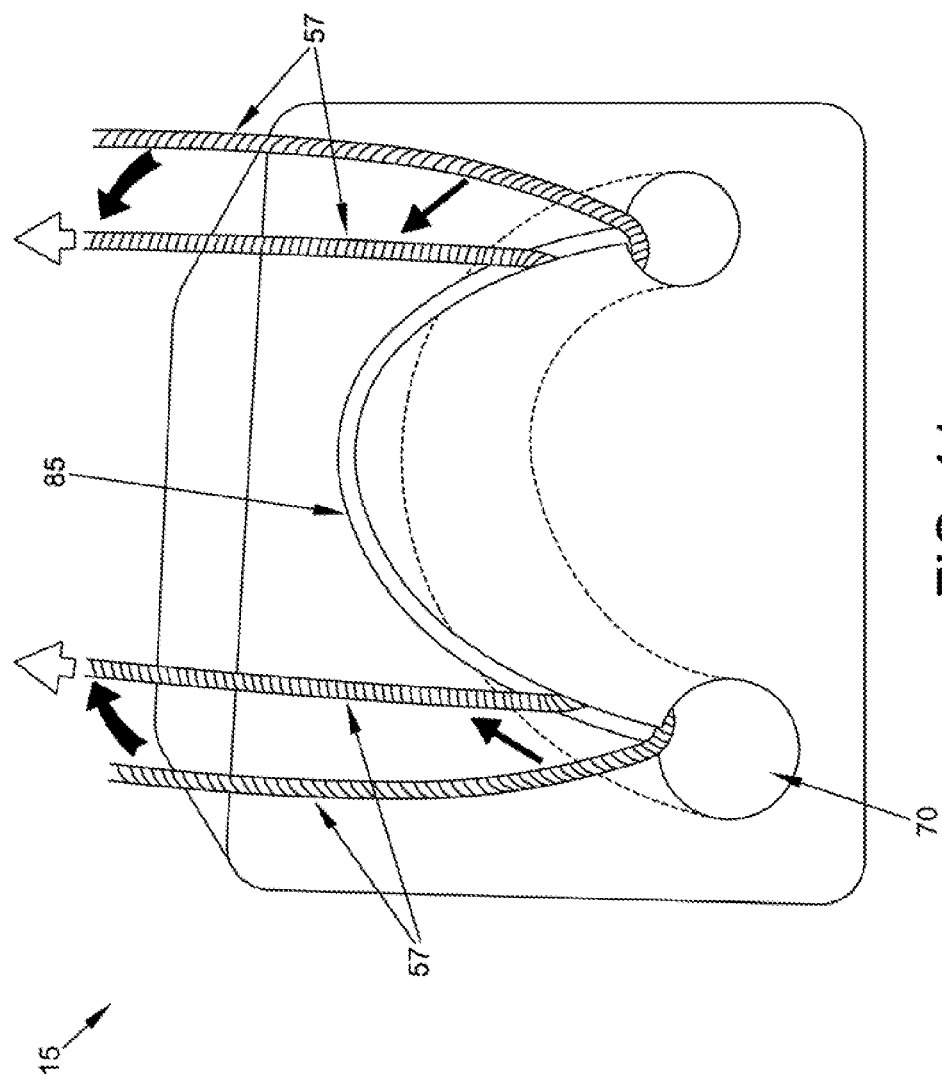
FIG. 11 is a schematic view illustrating the removal of the loop strand of filament through the filament release window of the knot box.

Once the knot has been formed on the post strand of filament, the knot may be removed from the knot box by grasping both loop strand of filament 57 and the post strand of filament and gently pulling the two strands out of the knot box, thereby allowing loop strand of filament 57 to exit through filament release window 85. More particularly, and looking now at FIG. 11, once tension is released from the long axis of loop strand of filament 57, the two ends of the loop strand of filament are drawn so as to cause the loop strand of filament 57 to move toward, and then out, filament release window 85. This movement allows the newly formed knot to "fall" out of the knot box, thereafter only requiring dressing and positioning to complete the knot. The term "dressing" a knot generally refers to arranging the segments of a finished knot so that the segments of the finished knot lie where the segments are supposed to, and do not cross each other where the segments are not supposed to. Dressing a knot is a normal activity to perform after a knot has been formed and is generally not considered part of knot formation.

It is important to note that if care is not taken to properly position the filament release window 85 relative to second pathway 70 when the knot box is being manufactured, the loop strand of filament 57 may unintentionally escape from the second pathway before the knot is fully formed, thereby causing the formation of the knot to fail. If, on the other hand, filament release window 85 is not provided in the second pathway at all, the knot has no way to escape from the second pathway after it is has been formed.

Figure 12:
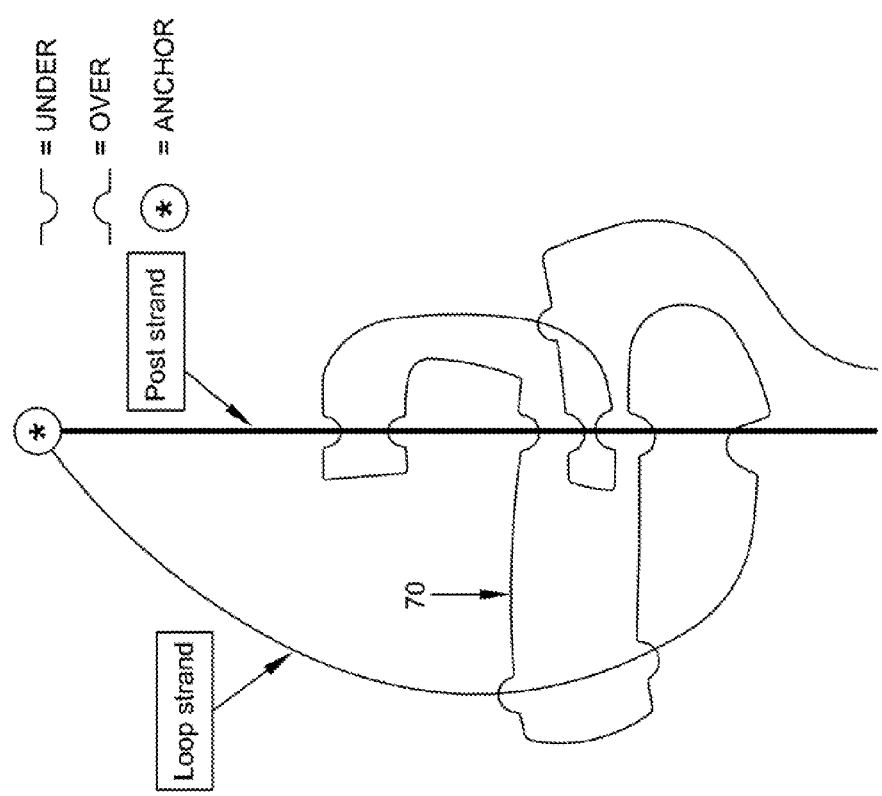
FIG. 12 is a schematic view illustrating an exemplary path that the loop strand of filament may take over and under a post strand of filament in order to form a knot.

Although the foregoing description describes the formation of a sliding, locking knot, it is important to note that many different kinds of sliding knots may be formed with the system of the present invention. See, for example, FIG. 12, which shows an alternative exemplary second pathway 70 that loop strand of filament 57 may take with respect to a post strand of suture in order to form a different knot.

Figure 13:
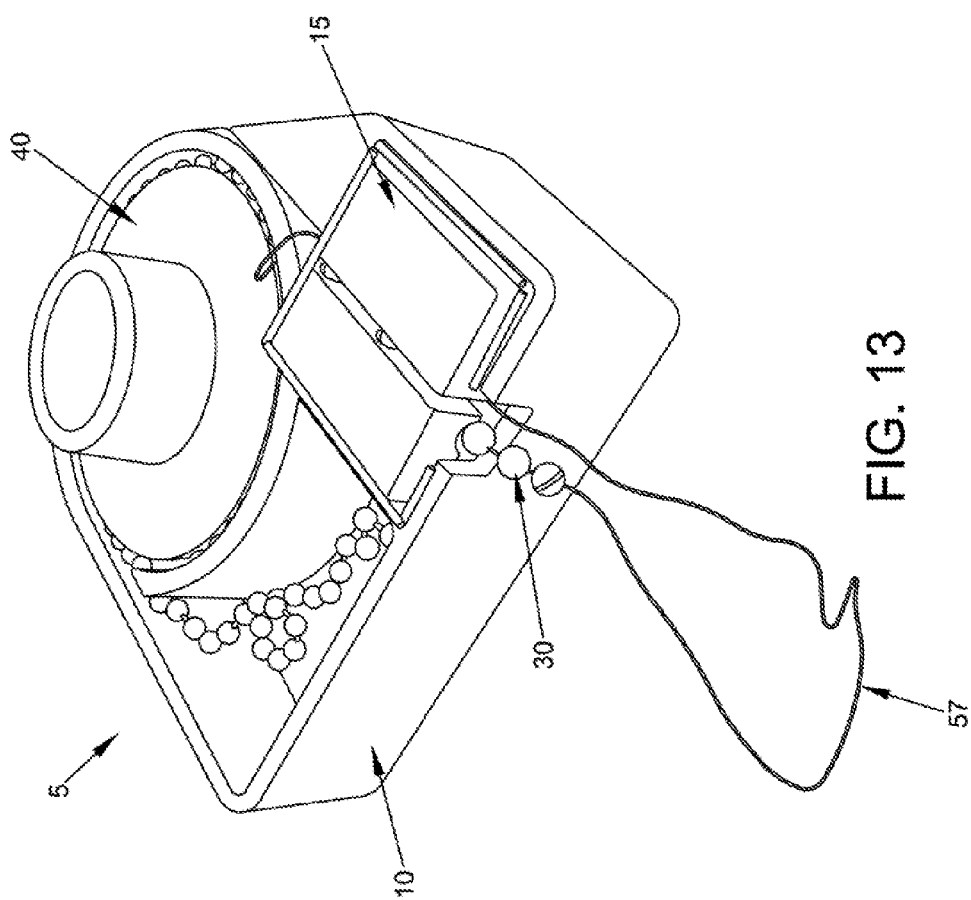
FIG. 13 is a view illustrating a table-top version of the system shown in FIG. 1.

In the foregoing description, system 5 has been described in the context of a hand-held device. However, it is important to note that the same features of system 5 may be provided in the form of a table-top device for use by a manufacturer in order to form a pre-tied knot in suture or filament. See, for example, FIG. 13 which shows a table-top version of the system.

Furthermore, in the foregoing description, a manually-operated rotary dial 40 is provided for moving shuttle 30. However, it will be appreciated that other advancing and retracting mechanisms, included powered advancing and retracting mechanisms or spring-assisted mechanisms, may be provided for moving shuttle 30.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An apparatus for forming a knot, the apparatus comprising:
   a first pathway for receiving a first element, and a second pathway for receiving a second element, wherein the first pathway has a configuration which corresponds to a path to be followed by the first element and the second pathway has a configuration which corresponds to path to be followed by the second element, respectively, in order to form a knot;
   a shuttle for moving the second element;
   a mechanism for moving the shuttle through the second pathway, whereby, when the first element is received in the first pathway and the second element is connected to the shuttle, movement of the shuttle through the second pathway causes the second element to be moved through the second pathway so as to form a knot around the first element;
   a first assembly comprising the shuttle for moving the second element, and the mechanism for moving the shuttle through the second pathway; and
   a second assembly comprising the first pathway for receiving the first element and the second pathway for receiving the second element;
   wherein the first assembly and the second assembly are connected together so that the shuttle may be passed from the first assembly to the second assembly in order to carry the second element through the second pathway of the second assembly, thereby forming a knot around the first element; and
   wherein the first assembly further comprises a rotary dial for advancing the shuttle out of the first assembly and retracting the shuttle into the first assembly.

2. The apparatus according to claim 1 wherein the first assembly comprises a shuttle reservoir for housing the shuttle.

3. The apparatus according to claim 1 wherein the first assembly comprises a first attachment mechanism and the second assembly comprises a second, complementary attachment mechanism for securing the second assembly to the first assembly.

4. The apparatus according to claim 1 wherein the shuttle comprises a strand of spheres having a filament attachment mechanism formed at one end of the shuttle, and further wherein the filament attachment mechanism comprises an eyelet.

5. The apparatus according to claim 1 wherein the first pathway comprises a straight path through a center portion of the second assembly, and the second pathway comprises a pattern configured to pass over and under the first pathway so as to form a knot on the first element.

6. The apparatus according to claim 5 wherein the first pathway comprises a filament-engaging element for securing the first element in the first pathway.

7. The apparatus according to claim 5 wherein the second pathway comprises an opening for releasing the second element from the second pathway after a knot has been formed around the first element.

8. A method for forming a knot, the method comprising:
   providing apparatus comprising:
      a first pathway for receiving a first element, and a second pathway for receiving a second element, wherein the first pathway has a configuration which corresponds to a path to be followed by the first element and the second pathway has a configuration which corresponds to a path to be followed by the second element, respectively, in order to form a knot;
      a shuttle for moving the second element;
      a mechanism for moving the shuttle through the second pathway, whereby, when the first element is received in the first pathway and the second element is connected to the shuttle, movement of the shuttle through the second pathway causes the second element to be moved through the second pathway so as to form a knot around the first element;
      a first assembly comprising the shuttle for moving the second element, and the mechanism for moving the shuttle through the second pathway; and
      a second assembly comprising the first pathway for receiving the first element and the second pathway for receiving the second element;
      wherein the first assembly and the second assembly are connected together so that the shuttle may be passed from the first assembly to the second assembly in order to carry the second element through the second pathway of the second assembly, thereby forming a knot around the first element;
   passing the first element through the first pathway;
   advancing the shuttle into the second pathway;
   securing the second element to the shuttle; and
   retracting the shuttle, with the second element attached thereto, through the second pathway so that the second element is maneuvered around the first element, thereby forming a knot around the first element;
   wherein the shuttle is advanced into the second pathway and retracted back through the second pathway by rotating a rotary dial on the first assembly.

9. The method according to claim 8 further comprising removing the knot from the second assembly.

10. An apparatus for forming a knot, the apparatus comprising:
    a first pathway for receiving a first element, and a second pathway for receiving a second element, wherein the first pathway has a configuration which corresponds to a path to be followed by the first element and the second pathway has a configuration which corresponds to a path to be followed by the second element, respectively, in order to form a knot;
    a shuttle for moving the second element;
    a mechanism for moving the shuttle through the second pathway, whereby, when the first element is received in the first pathway and the second element is connected to the shuttle, movement of the shuttle through the second pathway causes the second element to be moved through the second pathway so as to form a knot around the first element;

a first assembly comprising the shuttle for moving the second element, and the mechanism for moving the shuttle through the second pathway; and a second assembly comprising the first pathway for receiving the first element and the second pathway for receiving the second element wherein the first assembly and the second assembly are connected together so that the shuttle may be passed from the first assembly to the second assembly in order to carry the second element through the second pathway of the second assembly, thereby forming a knot around the first element;

wherein the first assembly further comprises a monitor for controlling an extent to which the shuttle is advanced out of the first assembly and retracted into the first assembly.

11. An apparatus for forming a knot, the apparatus comprising:

a first pathway for receiving a first element, and a second pathway for receiving a second element, wherein the first pathway has a configuration which corresponds to a path to be followed by the first element and the second pathway has a configuration which corresponds to a path to be followed by the second element, respectively, in order to form a knot;

a shuttle for moving the second element;

a mechanism for moving the shuttle through the second pathway, whereby, when the first element is received in the first pathway and the second element is connected to the shuttle, movement of the shuttle through the second pathway causes the second element to be moved through the second pathway so as to form a knot around the first element;

a first assembly comprising the shuttle for moving the second element, and the mechanism for moving the shuttle through the second pathway; and a second assembly comprising the first pathway for receiving the first element and the second pathway for receiving the second element wherein the first assembly and the second assembly are connected together so that the shuttle may be passed from the first assembly to the second assembly in order to carry the second element through the second pathway of the second assembly, thereby forming a knot around the first element;

wherein the shuttle comprises a strand of spheres having a filament attachment mechanism formed at one end of the shuttle;

wherein the filament attachment mechanism comprises a three-sided cleat.

\* \* \* \* \*